(12) United States Patent
Renshaw et al.

(10) Patent No.: US 6,630,127 B2
(45) Date of Patent: Oct. 7, 2003

(54) METHOD FOR ASSESSING CORTICAL RESPONSE TO BLUE LIGHT

(75) Inventors: Perry F. Renshaw, Arlington, MA (US); Ronald L. Cowan, Medford, MA (US); Blaise de.B. Frederick, Watertown, MA (US)

(73) Assignee: The McLean Hospital Corporation, Belmont, MA (US)

( * ) Notice: Subject to any disclaimer, the term of this patent is extended or adjusted under 35 U.S.C. 154(b) by 0 days.

(21) Appl. No.: 09/881,182

(22) Filed: Jun. 13, 2001

(65) Prior Publication Data

US 2002/0034472 A1 Mar. 21, 2002

Related U.S. Application Data

(60) Provisional application No. 60/211,059, filed on Jun. 13, 2000.

(51) Int. Cl.[7] .......................... A61B 5/055; A61K 51/00
(52) U.S. Cl. ......................... 424/9.3; 424/9.1; 424/9.2
(58) Field of Search ................... 424/9.1, 9.3; 600/310, 600/410, 473, 476

(56) References Cited

U.S. PATENT DOCUMENTS

| 5,632,276 A | 5/1997 | Eidelberg et al. ........ 128/653.1 |
| 5,699,798 A | 12/1997 | Hochman et al. ........ 128/653.1 |

FOREIGN PATENT DOCUMENTS

| WO | WO 99/66830 | 12/1999 |

OTHER PUBLICATIONS

Chen, Wei et al., "Spatial and Temporal Differentiation of fMRI BOLD Response in Primary Visual Cortex of Human Brain During Sustained Visual Simulation," *MRM* 39:520–527, (1998).

Chen, Yin Ching I. et al., "Detection of Dopaminergic Neurotransmitter Activity using Pharmacologic MRI: Correlation with PET, Microdialysis, and Behavioral Data," *Magnetic Resonance in Medicine* 38:389–398, (1997).

Howard, R. J. et al., "Functional Echoplanar Brain Imaging Correlates of Amphetamine Administration to Normal Subjects and Subjects with the Narcoleptic Syndrome," *Magnetic Resonance Imaging* 14:1013–1016, (1996).

Kwong, Kenneth K. et al., "Dynamic Magnetic Resonance Imaging of Human Brain Activity During Primary Sensory Stimulation," *Proc. Natl. Acad. Sci. USA* 89:5675–5679, (1992).

Mattay, Venkata S. et al., "Effects of Dextroamphetamine on Cognitive Performance and Cortical Activation," *NeuroImage* 12:268–275, (2000).

Nguyen, Tuong V. et al., "Detection of the Effects of Dopamine Receptor Supersensitivity Using Pharmacological MRI and Correlations with PET," *Synapse* 38:57–65, (2000).

Renshaw, Perry F. et al., "Greater Hemodynamic Response to Photic Stimulation in Schizophrenic Patients: An Echo Planar MRI Study," *Am. J. Psychiatry* 151:1493–1495, (1994).

*Primary Examiner*—Michael G. Hartley
(74) *Attorney, Agent, or Firm*—Clark & Elbing LLP (57) ABSTRACT

The invention provides methods for assessing central nervous system function and diagnosing central nervous system disorders in a human, and for evaluating therapeutic agents that affect central nervous system neurotransmitter function. The invention uses cortical imaging methods to assess changes in visual system processing, and correlates these changes to central nervous system function.

13 Claims, 4 Drawing Sheets

METHOD FOR ASSESSING CORTICAL RESPONSE TO BLUE LIGHT

RELATED APPLICATIONS

This application claims priority from U.S. Provisional Application No: 60/211,059, filed Jun. 13, 2000.

STATEMENT AS TO FEDERALLY SPONSORED RESEARCH

This invention was funded by grants DA09448, DA00366-01, and DA00343 from the National Institute on Drug Abuse. The government has certain rights in the invention.

FIELD OF THE INVENTION

This invention relates to central nervous system function.

BACKGROUND OF THE INVENTION

Although disorders such as Parkinson's disease, attention deficit disorder, schizophrenia, substance abuse, and mood and anxiety disorders generally involve imbalances in central nervous system functioning, the underlying neurological mechanisms of these diseases are poorly understood, with a corresponding dearth of suitable diagnostic methods and pharmacological therapies.

Blood oxygen level dependent functional magnetic resonance imaging (BOLD fMRI), near infrared optical imaging, and emission tomography methods have been used to assess cortical function. The BOLD fMRI method for studying stimulus-induced brain activity changes uses activity-dependent increases in local blood flow, with resultant decreases in the local deoxyhemoglobin concentration as a surrogate marker for increased local neuronal activity, and has been used to analyze visual cortical function. For example, visual stimulus-induced occipital cortical BOLD signal change has been shown to be dependent on gender and age, and to be influenced by disease processes such as schizophrenia. In addition, stimulus-induced occipital cortical activation is altered during the administration of exogenous substances, such as amphetamine, cocaine, and ethanol.

It would be useful to efficiently diagnose disorders of the central nervous system, and to evaluate effective pharmacological therapies for such disorders.

SUMMARY OF THE INVENTION

The invention features methods of assessing and diagnosing central nervous system function in a human subject.

In one aspect, the invention provides a method of assessing central nervous system function in a human subject by subjecting the subject to a blue light stimulus and performing cortical imaging, for example, functional magnetic resonance imaging, near infrared optical imaging, or emission tomography, on the subject. In a preferred embodiment, the method further includes treating the subject with a therapeutic agent for affecting central nervous system dopamine function, to assess the efficacy of the agent.

In another aspect, the invention provides a method of diagnosing a central nervous system disorder in a human subject by subjecting the subject to a blue light stimulus and performing cortical imaging, for example, functional magnetic resonance imaging, near infrared optical imaging, or emission tomography, on the subject. In preferred embodiments, the central nervous system disorder includes a disorder of central nervous system dopamine function, e.g., schizophrenia, Parkinson's disease, attention deficit hyperactivity disorder, substance abuse disorders, or mood and anxiety disorders (such as major depression or bipolar disorder).

In a preferred embodiment of both aspects of the invention, the blue light stimulus is compared to a light stimulus of a different color (e.g., red or green).

The methods, as are described in detail below, offer a wide range of advantages and applications. Other features and advantages of the invention will be apparent from the following detailed description.

By "central nervous system function" is meant any process responsible for, or mediating, affect, mood, behavior, cognition, perception, sensation, brain activity, or motor behavior.

By "central nervous system disorder" is meant any disease, pathological condition, or disorder, either acquired or genetically inherited, that adversely affects central nervous system function.

By "blue light stimulus" is meant a light stimulus of about wavelength 430–500 nm.

By "red light stimulus" is meant a light stimulus of about wavelength 640–700 nm.

By "treating" is meant the medical management of a patient with the intent that a cure, amelioration, or prevention of a dependency or a relapse or associated disease, pathological condition, or disorder will result. This term includes active treatment, that is, treatment directed specifically toward improvement of the dependency or associated cure of a disease, pathological condition, or disorder, and also includes causal treatment, that is, treatment directed toward removal of the cause of the dependency or associated disease, pathological condition, or disorder. In addition, this term includes palliative treatment, that is, treatment designed for the relief of symptoms rather than the curing of the dependency, disease, pathological condition, or disorder; preventive treatment, that is, treatment directed to prevention of the dependency or associated disease, pathological condition, or disorder; and supportive treatment, that is, treatment employed to supplement another specific therapy directed toward the improvement of the dependency or associated disease, pathological condition, or disorder. The term "treating" also includes symptomatic treatment, that is, treatment directed toward constitutional symptoms of the dependency or an associated disease, pathological condition, or disorder.

By "therapeutic agent" is meant a compound that is known to, or is proposed to, affect central nervous system neurotransmitter function. In general, a therapeutic agent is one that is used for treating neurologic, psychiatric, or substance abuse disorders.

By "affecting" is meant changing, either by decreasing or by increasing.

DETAILED DESCRIPTION OF THE INVENTION

The present invention features methods for assessing central nervous system function and diagnosing central nervous system disorders in a human, and for evaluating therapeutic agents that affect central nervous system neurotransmitter function. Changes in central nervous system neurotransmitter function occur in conjunction with changes in visual system processing, and these visual system changes are linked to alterations in higher brain functions. The invention provides a baseline for average responses, in humans, to red and blue light at varying intensities by using methods for assessing cortical function, for example, functional magnetic resonance imaging (e.g., BOLD fMRI), near infrared optical imaging, or emission tomography, as a non-invasive probe of human neurophysiology. Such methods provide powerful tools to assess intrinsic or exogenously-induced neurotransmitter-specific changes in central nervous system activity.

Studies of color and frequency responses according to the invention can be used in assays for specific neural system or neurotransmitter system function, for example, for studying dopamine function to diagnose neurologic, psychiatric, substance abuse, or mood and anxiety disorders, or to diagnose any disorder characterized by impaired central nervous system neurotransmitter (e.g., dopamine) function. Blue light response can be compared to those obtained with a light stimulus of a different color, for example, a red or green light stimulus. The response to blue light (in comparison with, for example, the response to red light) can be used in diagnosing central nervous system disorders, including those of altered dopaminergic function (e.g., schizophrenia, Parkinson's disease, and attention deficit hyperactivity disorder).

Specific therapeutic agents (e.g., neurotransmitter agonist/antagonist medications such as amphetamines) may be used to examine the specificity of the neurotransmitter response. In addition, the method of the present invention is used to monitor the effects of treatment with therapeutic agents that affect central nervous system neurotransmitter function, and to assess or demonstrate the effects of potential therapeutic agents at specific doses.

The BOLD fMRI signal change in occipital cortex, following photic stimulation, is determined by a large number of factors. The known neuronal elements influencing the response are the retina (including photoreceptors, intrinsic neurons, and ganglion cells), the lateral geniculate nucleus (including projections to V1 and intrinsic neurons), and the neurons of V1 (including the layer IV neurons that are the primary targets of the LGN projection as well as numerous vertical and lateral intrinsic connections). Vascular elements influencing the BOLD signal include the size and number of vessels, their proximity to the region of interest, and degree of coupling between local neuronal activity and blood flow. Hematocrit also influences the BOLD signal.

The following examples are provided for the purpose of illustrating the invention and should not be construed as limiting.

EXAMPLE 1

Measured Response to Light in Human Primary Visual Cortex Subjects

Thirty-seven volunteers (20 male, 17 female) aged 20 to 39 participated in a total of 55 functional Magnetic Resonance Imaging (MRI) scans. Some subjects participated in more than one scan. Subjects were screened only with regard to contraindications for MRI scanning (i.e., implanted electrical devices, surgically or traumatically implanted metal objects, or claustrophobia). Females were instructed to forego scanning if they felt there was a possibility of pregnancy, but were not tested for pregnancy. Subjects were not screened with regard to psychiatric status, medication usage, menstrual cycle phase, medical status, or psychoactive substance use.

Magnetic Resonance Imaging

MRI scans were performed on a 1.5 Tesla (T) Signa (General Electric, Milwaukee, Wis.) whole body magnetic resonance image configured with an Instascan (Advanced NMR, Wilmington, Mass.) whole-body echo planar imaging (EPI) coil.

Structural imaging: Anatomical brain structural imaging was performed on each subject in the sagittal, coronal, and oblique planes to provide matched anatomical sections with detail for cross-referencing functional to anatomical images. Using a standard quadrature head coil, T1 volumetric 3D Spoiled Gradient Recall (SPGR) images were obtained with parameters of flip angle 45 degrees, TR 35 mS, TE 5 mS, slice thickness 1.5 mm, field of view (FOV) 24×24 cm, matrix size 256×256 pixels for an in plane resolution of 0.94 mm.

Functional imaging: For BOLD imaging, gradient echo EPI images collected in an oblique plane parallel to the calcarine fissure were used to assess photic stimulation-induced BOLD signal changes. Three (3) to twelve (12) locations of 5 mm thickness with 0 mm skip were obtained to include the calcarine cortex and adjacent regions. Acquisition parameters were TR=2 or 3.5 S, flip angle=75 or 82 degrees respectively, matrix=128×64 voxels, FOV −40×20 cm, 3.3 mm in plane resolution. TR 2.5, 120 images, TR 3.5, 75 images were obtained at each location using a 5 inch receive-only surface coil. During the BOLD acquisitions, periods of darkness alternated with periods of photic stimulation as described below. Images were stored as digital data and transferred to an off-line storage and analysis computer for post-acquisition processing and statistical analysis. Images were motion-corrected prior to analysis using a Decoupled Automated Rotational and Translational (DART) program.

Data Analysis fMRI Data Analysis: Image analysis was performed using Functional Analysis Tool (FAT) software. Increased signal intensity in BOLD fMRI images was used as a marker for regional neuronal activation. BOLD signal was analyzed using the statistical mapping method, by applying an automated comparison method to perform a Student's test on a pixel-by-pixel basis of signal during periods defined as baseline or BOLD signal increase. The pixels in a region of interest were used to calculate the magnitude of BOLD signal change. Regions of interest were designed to yield a measure of the zone of best activation within right and left V1. A 1×4 pixel array oriented with the long axis parallel to the inter-hemispheric fissure was drawn within the region having the best activation according to number or intensity of activated pixels. No regions containing significantly negatively correlated pixel activation were drawn. To avoid labeling non-statistical activation as equal to zero in brain regions where there was no detectable signal activation, a region of interest was drawn in a comparable location to activated regions in other slices within V1.

Photic Stimulation: Color photic stimulation was delivered via a custom-designed set of stimulus goggles with three independently-controlled sets of light emitting diodes (LEDs) that emit light at 470 nm (blue, Panasonic LNG992CFBW), 570 nm (green, AND AND183HGP), and 660 nm (red, AND AND180CRP) and can flash independently or in any combination. To avoid introducing noise into the magnetic resonance system, the LEDs and all control electronics were located outside the magnet bore; the goggles were fed by a 20-foor long fiber optic bundle (South Coast Fiber Optics, Alachua, Fla.). Each eye of the goggles had a 6 row by 8 column matrix of pixels. Each column could be individually controlled to vary intensity and flash patterns (individual eye, individual hemifield, moving vertical bars, etc.). The optical wavelengths were chosen to match the response curves of the three color cones in the human eye; each frequency excites one type of cone preferentially. To standardize the LED intensities according to a physiological parameter (percent BOLD signal change), the threshold detectable BOLD signal increase in response to each color LED was estimated from early data from a few samples, and LED intensity (contrast) was scaled in relation to the threshold. Blue LED intensity was twice that of red LED stimulation. Blue LED intensities ranged from 0.12 lux to 620 lux. Red LED intensities ranged from 0.06 to 320 lux. For all experiments in this study, the entire 6 by 8 fiber array was flashed for each stimulus period.

Subjects were placed in the scanner with the surface coil in place and the photic stimulation goggles were placed on the head and stabilized. To maintain constant distance between the eye and the light source, the eyepieces of the goggles were in contact with the skin in each subject. Goggles were adjusted to maximize comfort and angle of view. The period of photic stimulation, after accounting for a hemodynamic delay of 3.5 seconds, was considered as the activation phase for BOLD signal acquisition. To determine the effect of the wavelength of the optical stimulus on the activation response, signal was analyzed for red and blue stimuli individually.

The use of goggles permitted the delivery of colored light against a background of essentially complete darkness, however, as the study progressed it was noted that the goggles were not completely light-opaque, introducing the potential for partial illumination of the background via ambient lighting. Ambient room lighting was not controlled and varied according to time of day (light penetrating a skylight) and combination of artificial room lighting (overhead, side, or gantry) lighting. This effect was not quantified but was generally constant within an experimental trial. This problem was corrected in later studies.

Determination of Threshold

The baseline activation characteristics of the BOLD fMRI response in the human visual cortex to red and blue light at varying intensities was established by comparing the response to red and blue photic stimuli in a group of healthy control subjects in terms of threshold for activation, slope of the activation response, and hemisphericity of the response. Baseline response parameters were established in a group of controls to enable the application of this technique to the study of individual brain function during the systematic manipulation of central nervous system dopaminergic activity. The analysis was restricted to primary visual cortex rather than higher-order visual areas (including color areas) to develop a method of assessing the synaptic integrity of visual transduction at the earliest stage of neocortical processing. As studies in intact humans are exceptionally complex, it is important to isolate the sensory transduction pathway in the simplest form possible with the present methodology. The present invention assesses primary visual cortical activation near threshold and at varying suprathreshold intensities of light, and also compares right and left visual cortical responses.

The first experimental series consisted of delivering low-intensity pulses of blue or red light with various LED intensity settings to determine threshold intensity for detectable BOLD activation in V1. Six male and six female subjects participated and each subject received three different intensities of both red and blue light. Three intensities were delivered in incremental order of intensity for one color, followed by three incremental order intensities in the other color. The choice of the first color order was arbitrary. Blue light intensities were 0.12, 1.2, and 6.2 lux. Blue light was delivered at 4 Hz for 1 subject and at 8 Hz for 11 subjects. Red light intensities were 0.06, 0.32 and 3.2 lux. Red light was delivered at 8 Hz for all subjects. Each trial consisted of 30 seconds on, 30 seconds off, 4 stimulus and 4 rest periods.

Determination of Intensity-Activation Relationships Above Threshold

To determine the effect of increasing intensities of light against a constant background illumination, a series of 6 intensities flashing at 8 Hz for a duty cycle of 30 seconds on, 30 seconds off, or 30 seconds on, 60 seconds off, were tested for red or blue light during a single experimental session. The LED intensity steps were chosen to provide a range of stimuli that were tolerated by subjects. A single color of light was delivered during a single session to minimize inter-subject variation across the six intensities of stimulation. The intensities were delivered in order of lowest to highest intensity to minimize potential adaptation or response fatigue, and to minimize potential for subject intolerance of prolonged scanner times. A total of 8 (3 female; 5 male) red and 11 (5 female; 6 male) blue light intensity series were performed. Six subjects participated in both the red and blue light stimulation, 8 subjects participated in one or the other but not both. The intensity series were designed so that the lowest intensity was the same as the highest intensity used in the threshold measurements. The higher intensity light data were combined with the lower intensity data from the threshold determinations to determine the best-fit line equation and statistical comparisons.

Statistical Analysis

Statistical analysis was performed using Stata, Version 6.0 (Stata Corporation, College Station, Tex.). Unpaired t-tests for unequal variances were used to compare age distribution by sex for each color. Statistical comparisons for the effect of color and brain hemisphere were performed using linear regression modeling. Results were reported as Z score and p value for testing the null hypothesis that the difference between the coefficients (beta) of the regression model equal zero. Mean activation across all intensities was compared using $Chi^2$ analysis. An alpha level of 0.05 was used as the cutoff for statistical significance for all tests.

Analysis of Threshold for Activation in V1

Threshold was defined as the stimulus intensity that would produce statistically significant positive activation in 50% of test subjects. This approach was used to develop an intensity measure that could be used across subjects. The application of this method may be limited by the inability to adjust the stimulus intensity and monitor activation during an experiment (due to the necessity of offline motion correction of images). Applying threshold estimates from preliminary data to the subjects allowed close approximation of the threshold for detectable activation to red light and provided data that allows refinement of the stimulus intensity for determining a more precise threshold for blue light. This approach allows for the application of objective criteria to the response measurement and provides a stimulus intensity-response baseline for comparison during experimental or disease-related alterations. The practical advantages of such an approach are numerous. By examining low-intensity stimuli, the ability to detect subtle alterations in stimulus-activation relationship is enhanced, subject fatigue (either physiologic or from exposure to bright light) is diminished, and changes in threshold can be compared to and potentially dissociated from changes in slope or maximum of the response. In contrast, many prior visual system studies using the BOLD fMRI technique used stimuli that produced maximum or near maximum activation.

For subjects in all trials receiving red light stimulation, the mean age was 22.4 years for female subjects, and 29.0 years for males. For subjects receiving blue light stimulation, the mean female age was 23.3 years, and the mean male age was 30.3. The mean age for males was significantly higher than for females in both cases, p<0.001, tested using unpaired t-test for unequal variances. The threshold for BOLD signal increase in V1 was determined by using LED intensities that were at the approximate threshold for detection. Based on preliminary analysis of 3–5 subjects, intensities were targeted so that, at threshold, approximately 50% of the subjects would show a positive is BOLD signal increase. The low intensity blue light (0.12 lux) produced positive BOLD signal increase in 11 of 12 (5/6 male, 6/6 female) subjects, while the low intensity red light (0.06) lux produced positive BOLD signal increase in 8 of 12 (4/6 male, 4/6 female) subjects, indicating that the red threshold intensity estimate was closer to the target than that for blue light. Analysis of the near-threshold responses by sex (Table 1) revealed that mean BOLD signal increase was not statistically different for red light, but was significantly lower in females for blue light.

TABLE 1

V1 BOLD signal increase to Red and Blue Light Near Threshold

| Color | Sex | Mean BOLD signal increase (+/− S.D.) |
| --- | --- | --- |
| Red | Female | 0.11% (0.15) |
|  | Male | 0.03% (0.18) |
| Blue* | Female | 0.14% (0.08) |
|  | Male | 0.52% (0.50) |

*significantly different, p = 0.015

Analysis of the Stimulus-intensity Versus Activation Curves

The overall BOLD response to all intensities for each color was best described by BOLD signal change versus the log of the stimulus intensity change. While potential confounders such as medication and diagnosis were not controlled for, the $R^2$ measures were exceptionally linear for both colors. The slope was less steep for the blue intensity-activation curve when compared to red. The maximum BOLD signal change values for the red and blue stimuli were not directly compared because a different maximum stimulus intensity value was used for the two colors. However, even at the higher stimulus intensity used for blue light, the average activation over the analysis regions was 2.30%, and for the red light, 3.26%, using a stimulus one half as intense as that used for blue light. The actual maximum BOLD signal change for each color was not determined because neither response curve showed a plateau suggesting saturation. A conservative explanation for this finding is the difference in blue versus red cone density: blue cones comprise an estimated 7% of the retinal cone population and red cones about 80%. An important caveat to any simplistic interpretation of these findings is that activation as measured by BOLD signal increase permits no conclusions regarding the proportion of excitatory or inhibitory neurons activated by a visual stimulus. Differences in the slope of the stimulus-activation curves are likely influenced by local and network synaptic connectivity, particularly lateral and vertical recurrent excitation and inhibition.

Figure 1A:
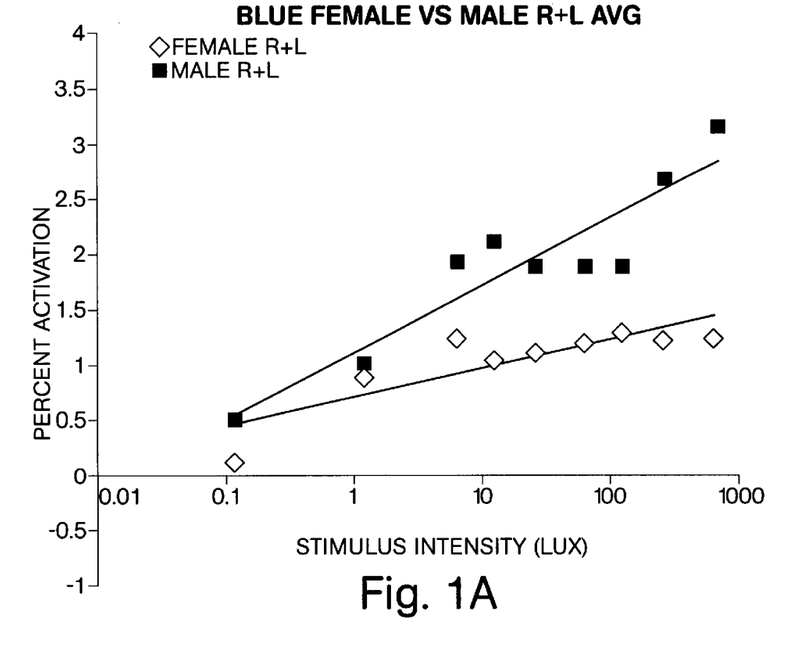
FIG. 1A is a graph of BOLD signal increase versus stimulus intensity in V1 for red light in males and females.
Figure 1B:
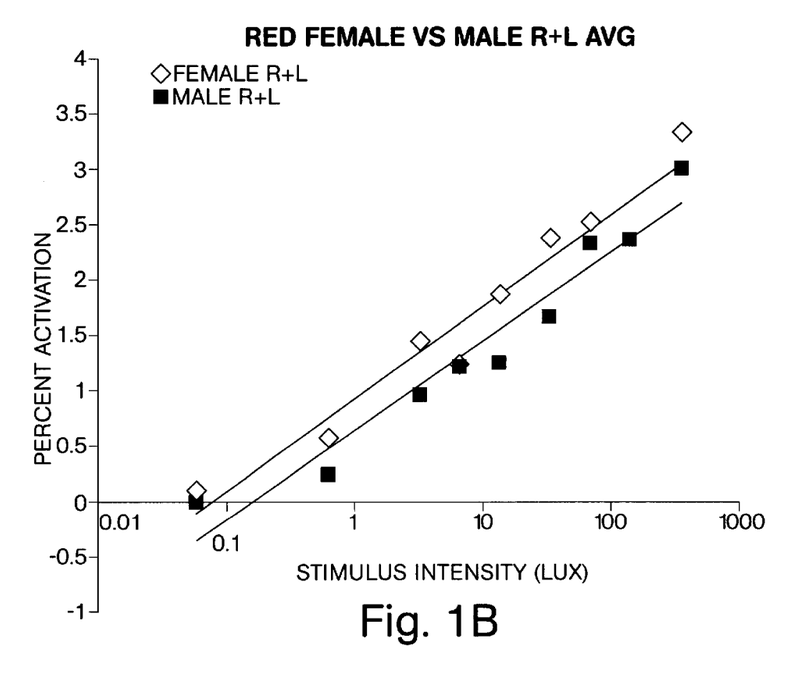
FIG. 1B is a graph of BOLD signal increase versus stimulus intensity in V1 for blue light in males and females.

An analysis of combined photic stimulation of all subjects at all intensities, including those near and above the threshold range, produced stimulus intensity versus BOLD signal change curves. Because of positive skewness, these response curves were modeled using a logarithmic transformation of the stimulus intentsity versus a non-transformed linear BOLD signal change response. The effect of sex or age on activation was significant for blue light response when each variable was considered alone in the regression model, but age showed no association with outcome after controlling for stimulus intensity. Conversely, the effect of sex remained significant in the combined model. Best-fit (least squares) regression equations were determined separately for the red and blue intensity-BOLD signal increase curves for grouped data for each sex. FIG. 1 is a graph of stimulus intensity versus BOLD signal increase in V1 for all nine intensity steps (data are pooled right and left V1 from all experiments) for red light (FIG. 1A; intensities were 0.06, 0.65, 3.2, 6.5, 13, 32, 65, 130, and 320 lux) and blue light (FIG. 1B; intensities were 0.12, 1.2, 6.2, 12, 25, 62, 120, 250, and 620 lux). The abscissa is the logarithmic scale of LED intensity in Lux; the ordinate is percent activation compared to baseline in a 1×4 pixel array from right calcarine cortex. The best-fit trend lines are superimposed. The best-fit equations for the red and blue intensity-BOLD signal change series are shown in Table 2.

TABLE 2

Stimulus Intensity BOLD signal response Curve by Sex and Color

| Color | Sex | Model | $R^2$ |
| --- | --- | --- | --- |
| Red | Female | y = 0.3687 Ln(x) + 0.9475 | 0.95 |
|  | Male | y = 0.3582 Ln(x) + 0.6519 | 0.94 |
| Blue* | Female | y = 0.1157 Ln(x) + 0.7219 | 0.72 |
|  | Male | y = 0.2683 Ln(x) + 1.1217 | 0.86 |

*significantly different slope and mean activation

Analysis of the Effect of Hemisphericity and Responses

The response in right hemisphere V1 was significantly higher for blue light and non-significantly higher for red light at the 0.05 level of significance in the pooled data (males and females). Activation data from a single color from all subjects were pooled for comparison of right versus left V1 response. Statistical analysis with linear regression modeling, using pooled data from all intensities, indicated that the coefficients for the right versus left side activation showed a non-significant trend for greater right-sided red light-induced V1 activation at an alpha level of 0.05 ($z=1.686$, $p=0.092$), and a significantly greater activation for right-sided blue light at an alpha level of 0.05 ($z=2.265$, $p=0.024$).

EXAMPLE 2
Effects of d-Amphetamine on Photic Activation to Blue Light

A human fMRI BOLD study was conducted using alternating red and blue photic stimulation to assess the differential effects of the dopamine-releasing drug d-amphetamine on the BOLD response in human primary visual cortex.

Subjects

Fifteen volunteers (5 male; 10 female) participated in 22 functional MRI scans. The volunteers were initially screened by phone questionnaires to rule out the presence of medical illness, psychiatric illness, or substance abuse. Upon arrival at the research laboratory, subjects were further screened with regard to contraindications for MRI scanning via the use of questionnaires and personal interviews with a physician. Urine pregnancy testing (for females) was performed with QuPid One Step Pregnancy Test (Stanbio Laboratory, Inc. San Antonio, Tex.). Subjects received breath alcohol analysis using the Alco Sensor III (Intoximeters, St. Louis, Mo.), and urine screen for psychoactive drug use (Triage Drugs of Abuse Panel, Biosite Diagnostics, San Diego, Calif.). Exclusion criteria for participation in the study were: 1) cardiovascular illness, 2) current DSM-IV defined (1) Axis 1 psychiatric or substance-related disorder, or history of DSM-IV defined psychotic disorder, 3) current use of psychoactive or vasoactive medications, 4) seizure disorder, 5) contraindications to MRI scanning, including presence of a cardiac-pacemaker, metallic implants or metallic foreign bodies, or claustrophobia, 6) positive urine drug screen or pregnancy test, 7) positive alcohol breathalyzer test. Seven subjects participated in both placebo and drug administration studies; 8 subjects participated in either placebo or drug administration studies. No subjects had positive urine drug or pregnancy screens and all had negative alcohol breath tests.

Experimental Protocol

Figure 2:
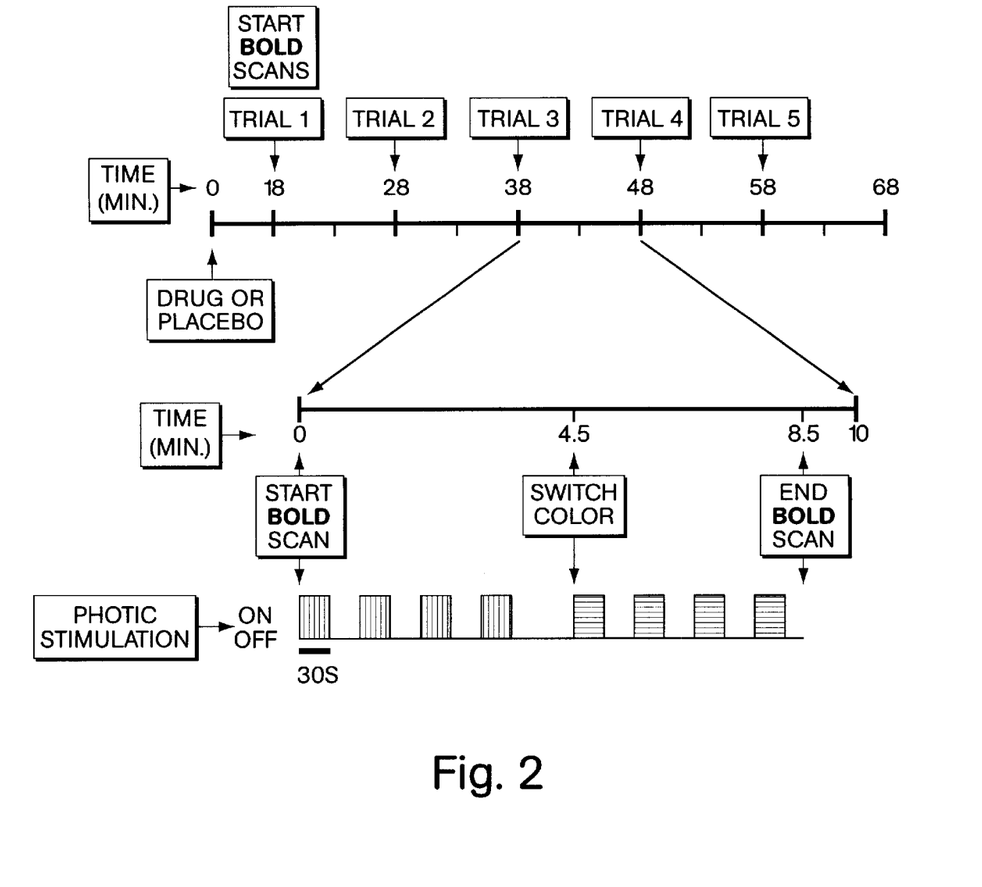
FIG. 2 is a diagrammatic representation of the d-amphetamine experimental protocol.

FIG. 2 is a diagrammatic representation of the photic stimulation and echo-planar imaging (EPI) protocol. Individual time epochs varied more than is illustrated, and actual time measures were used in statistical analyses. The upper portion of the figure depicts the time course of the experiment. Drug or placebo was administered orally at the time defined as 0 minutes. Subjects were then placed in the scanner, goggles were fitted, and baseline structural imaging scans were performed. Echo-planar imaging started at approximately 18 minutes and 5 trials were conducted. The middle of the diagram details a single trial. Within each trial, the start of the BOLD measurement (after discarding 4 dummy scans) was the zero time point. Each BOLD trial lasted 8 minutes 30 seconds, and images were collected at 2 S intervals. Red or blue photic stimulation started coincident with the onset of the BOLD trial (color order was varied, red was first in approximately half of all trials). The first four minutes of a trial consisted of a 4-minute epoch of red or blue photic stimulation. Each 4-minute epoch consisted of four 30 S periods of photic stimulation alternating with 4 30 S periods of darkness. An additional 30 S period of darkness was imposed during the color switch portion of the trial, and the 4-minute sequence of photic stimulation alternating with darkness was repeated for the second color. The total interscan time was approximately 10 minutes to account for post-imaging processing and storage.

Drug Administration

Subjects received lactose placebo tablets or drug tablets (2.5 mg d-amphetamine sulfate (Dexedrine, SmithKline Beecham Pharmaceuticals, Philadelphia, Pa.)). The 2.5 mg tablet was prepared by halving a 5 mg tablet. A low dose of amphetamine was chosen to minimize the potential for amphetamine-induced movement. Subjects were blind to placebo or drug status. Investigators were not blind to drug status in the administration phase, but were blinded during the analysis phase.

Physiological Monitoring

Subject's cardiac rate and rhythm and oxygen saturation were monitored continuously during each experiment and blood pressure measurements were obtained at approximately 5-minute intervals throughout the experiment using an automated blood pressure cuff (In Vivo Research, Orlando, Fla.).

Magnetic Resonance Imaging

MR scans were performed on a 1.5 Tesla (T) Signa Echo-Speed (General Electric, Milwaukee, Wis.) whole body magnetic resonance scanner (level 5.8). Anatomical brain imaging was performed on each subject in the sagittal, coronal and oblique axial planes to provide matched anatomical sections with detail for cross-referencing functional to anatomical images. Using a standard quadrature head coil, T1-weighted volumetric 3D Spoiled Gradient Recall (SPGR) images were obtained with parameters of: Flip angle=5 degrees, TR=300 ms, TE=9 ms, slice thickness=5 mm, field of view (FOV)=20×20 cm, matrix size 256×192 pixels for an in plane resolution of 0.95 mm. For BOLD imaging, gradient echo EPI axial images collected in an oblique plane parallel to the calcarine fissure were used to assess photic stimulation-induced BOLD signal changes. Three locations of 5 mm thickness with 0 mm skip were obtained to include the calcarine cortex and adjacent regions. Acquisition parameters were TR=2 S, flip angle=90 degrees, matrix=64×64 pixels FOV=20×20 cm, 3×3 mm in-plane resolution. 256 images were obtained at each location using a 5 inch receive-only surface coil. During the BOLD acquisitions, periods of darkness alternated with periods of photic stimulation. Images were corrected for in-plane subject motion before analysis using the 2-dimensional Decoupled Automated Rotation and Translation (DART) registration algorithm (Maas LC et al., Magnetic Resonance in Medicine 1997; 37: 131–139).

Photic Stimulation

Color photic stimulation was delivered via a custom-designed set of stimulus goggles (Frederick B de B et al., 6th Annual Meeting of the Organization for Human Brain Mapping. 2000: San Antonio, Tex.). The goggles have three sets of light emitting diodes (LEDs) that emit light at 470 nm (blue), 570 nm (green), and 660 nm (red), which can flash independently or in any combination. The optical wavelengths were chosen to match the response curves of the three color cones in the human eye; each frequency exciting one type of cone preferentially (Gouras P and Zrenner E. Vision Research 1981; 21: 1591–1598). The LED's and all control electronics were located outside of the magnet bore. The goggles were fed by a 20-foot long fiber optic bundle (South Coast Fiber Optics, Alachua Fla.). Each eye of the goggles had a 6-row by 8-column matrix of pixels.

Each color trial consisted of 8 Hz flash rate light delivered for 30 S on, 30 S off, 4 stimulus and 4 rest periods. Trials were repeated a total of 5 times (FIG. 2). Intensity was varied by changing flash duty cycle (within a 30 S stimulation period, all flashes were extremely short, 5 mS or less). Blue and red LED intensities were 0.12 lux as measured using a lux meter (Extech Instruments Foot Candle/Lux Meter, Waltham, Mass.) at the operational distance used for subject stimulation. For all experiments in this study, the entire 6 by 8 pixel array was flashed in each eye for each stimulus period against a dark background. Signal was analyzed for red and blue stimuli individually. All experiments were conducted in a darkened room.

Image Analysis

Figure 3:
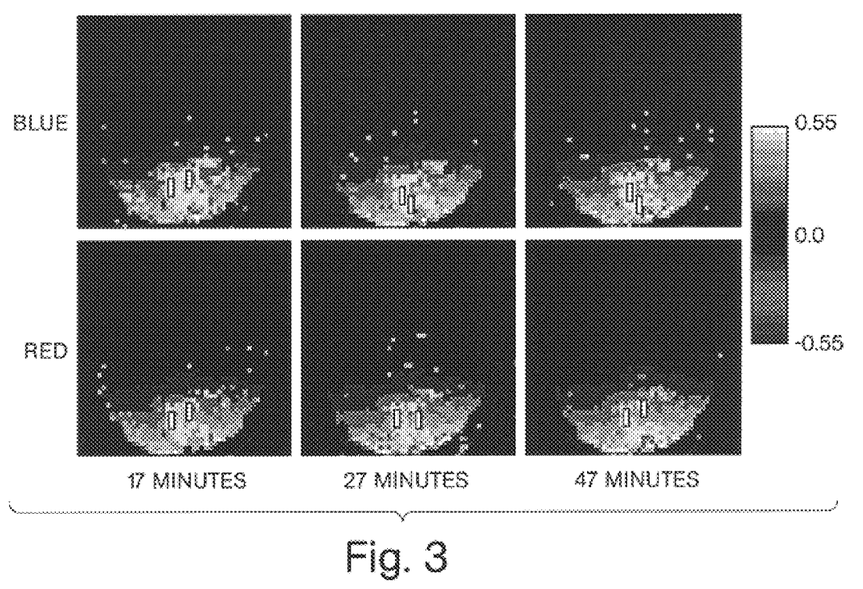
FIG. 3 is a representative correlation-map display of BOLD signal change through axial oblique sections of visual cortex from a single subject who received drug. Green rectangles represent the Region of Interest (ROI) from right and left V1, which is placed in maximally activated 1×4 pixel region. The top row is subject response to fixed intensity blue light stimulation over time following ingestion of 2.5 mg d-amphetamine. The bottom row is same subject showing response to red light in the same experiment. Time post-drug increases from left to right. The calibration bar displays pseudo-color overlay scale as corresponding to correlation coefficient.

All image analysis was performed blind to experiment and subject identification, trial condition (lactose placebo versus d-amphetamine drug) and to trial order. Image analysis was performed using software developed at our center. An automated mapping procedure (Maas LC et al., American Journal of Psychiatry 1998; 155: 124–126) was used to compare the correlation between the time course of signal change in a pixel with that of the time course of the photic stimulus according to the correlation coefficient detection method of Bandettini et al., (Bandettini PA et al., Magnetic Resonance in Medicine 1993; 30: 161–173). Pixels whose correlation coefficient was above an arbitrarily chosen threshold (r=0.25) were identified and displayed using pseudo-color overlays of stepped changes in correlation. Color display is shown in FIG. 3.

Region of Interest (ROI) Determination

The ROI for this study was chosen in an attempt to study the physiologically most active sub-region (as defined by BOLD signal change) within right and left V1. The anatomical boundaries for V1 were determined as follows: The anterior boundary was the parieto-occipital sulcus. The posterior boundary was the occipital pole. The medial boundary was the interhemispheric fissure. The lateral boundary was determined for right and left sides as a maximum of 3 pixel widths lateral to the midline. Once the anatomical boundaries for V1 were determined, a 1×4 contiguous pixel region whose long dimension was oriented parallel to the interhemispheric fissure was drawn within right V1 and left V1 to circumscribe a 4 pixel region having the highest correlation coefficient as determined by the correlation map display (see FIG. 3 for an example of ROI). The magnitude of BOLD signal increase (activation) was determined as the percent change in the mean signal intensity within the ROI during the period of photic stimulation (average of signal from the 4 stimulation periods for each trial) compared to the mean baseline signal (average of signal from the 4 non-stimulus periods for each trial). A 1×4 pixel ROI was sensitive to small graded changes in BOLD signal within V1.

Statistical Analysis

Statistical analysis was performed using Stata, Version 6.0 (Stata Corporation, College Station, Tex.). Wald $Chi^2$ analysis with 1 degree of freedom was used to determine if there was an effect of drug on the mean activation across an average of all trials for each color (i.e. to compare red placebo and blue placebo means, red placebo means to red drug means, and blue placebo means to blue drug means). Linear regression modeling with robust estimation of standard errors was used to examine the effects of age and sex on BOLD signal change, and to determine if there was an effect of time following drug (time points were entered as the time of onset of a particular color trial following drug ingestion) on the mean signal change from the 1×4 region in right and left V1. Model fit was assessed using partial residual plot methods. An alpha level of 0.05 was used as the criterion for statistical significance for all tests.

Effect of Age and Sex on BOLD Signal Change

The mean age for the control group was 23.8 (S.D. 3.6) and for the drug group 25.6 (S.D. 5.0). There were no significant effects of age on BOLD signal change to red (Z=−0.474, P=0.635) or to blue (Z=−0.857, P=0.392) light stimulation for placebo or drug. Similarly, there were no significant effects of sex on BOLD signal change to red (Z=1.360, P=0.174) or to blue (Z=1.323, P=0.186) light stimulation.

V1 BOLD Signal Change to Iso-intense Red and Blue Light Stimulation: Placebo

To determine if iso-intense stimuli of blue and red light at 0.12 lux were equally effective at eliciting V1 BOLD signal change, the mean BOLD signal change in V1 was compared across all trials for combined right and left V1 for each color in the placebo condition. The mean BOLD signal increase to red light stimulation at 0.12 lux was 0.95% (S.D. 0.76). The mean BOLD signal increase to blue light stimulation at 0.12 lux, conversely, was 1.60% (S.D. 0.74). Wald $Chi^2$ comparison of the mean activations revealed a significant difference in the baseline (placebo condition) response to the two colors, with blue light eliciting a 68% greater BOLD signal increase than the corresponding intensity of red light (Wald $Chi^2$=52.00, P<0.0001).

V1 BOLD Signal Change to Blue Light Stimulation: Placebo Versus Drug

The mean BOLD signal change from the 1×4 ROI in right and left V1 was grouped across all trials for the drug and placebo condition to determine if d-amphetamine administration altered the mean BOLD signal change. For blue light, the overall mean was significantly different in the Wald $Chi^2$ analysis, with the mean BOLD signal change being 28% higher in the drug (2.04%) condition than in the placebo (1.60%) condition (Table 3).

TABLE 3

| | V1 BOLD signal change to Blue light stimulation | | | |
|---|---|---|---|---|
| Condition | Mean % BOLD signal change (all trials)* | S.D. | Wald $Chi^2$ | P |
| Drug (N = 13) | 2.04 | 1.12 | 31.20 | <0.0001 |
| Placebo (N = 9) | 1.60 | 0.74 | | |

Figure 4:
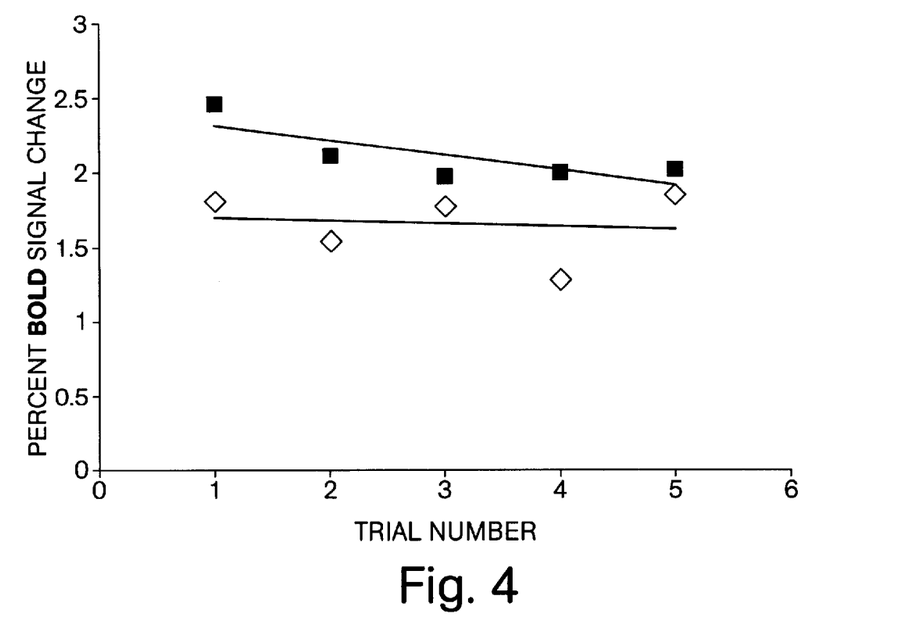
FIG. 4 is a graph of mean activation from right and left V1 from all subjects for blue light stimulation. The Y axis shows the percent signal change from baseline. The X axis shows the trial number. The solid squares represent data from the subjects who received drug, hollow diamonds represent data from the subjects who received placebo. The lines are least squares regression lines.

*significantly different mean activation across all trials for drug versus placebo condition To further characterize the time course of the effect of drug on the blue light response, grouped means were plotted as percent BOLD signal change versus trial number for the blue light placebo and drug conditions (FIG. 4). Because drug levels were expected to increase over time during the experiment, a linear regression analysis was used to determine if there was an effect of time following drug administration on the BOLD signal response to blue light. For the drug condition, there was a significant effect of time following drug administration on BOLD signal change (Z=−2.471, P=0.013) with decreasing BOLD signal over time. For the placebo condition, there was no significant effect of time on BOLD signal change (Z=−0.355, P=0.722).

V1 BOLD Signal Change to Red Light Stimulation: Placebo Versus Drug

For red light, the overall mean was also significantly different in the Wald $Chi^2$ analysis, with the mean BOLD signal change being 30% higher in the drug (1.24%) condition than in the placebo (0.95%) condition (Table 4).

TABLE 4

V1 BOLD signal change to Red light stimulation

| Condition | Mean % BOLD signal change (all trials)* | S.D. | Wald Chi$^2$ | P |
|---|---|---|---|---|
| Drug (N = 13) | 1.24 | 0.76 | 19.36 | <0.0001 |
| Placebo (N = 9) | 0.95 | 0.80 | | |

Figure 5:
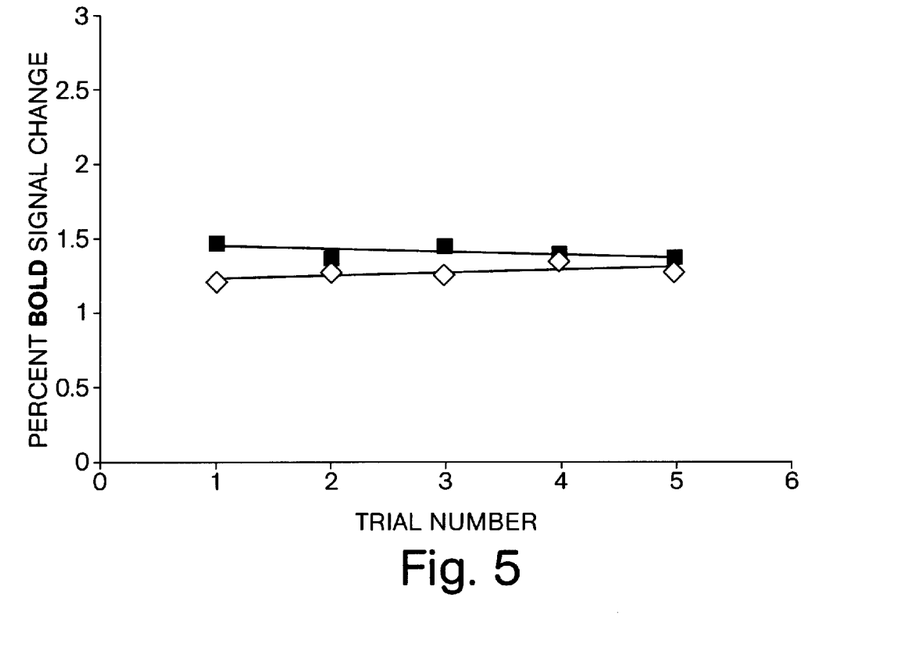
FIG. 5 is a graph of mean activation from right and left V1 from all subjects for red light stimulation. The Y axis shows the percent signal change from baseline. The X axis shows the trial number. The solid squares represent data from the subjects who received drug, hollow diamonds represent data from the subjects who received placebo. The lines are least squares regression lines.

*significantly different mean activation across all trials for drug versus placebo condition To further characterize the time course of the effect of drug on the red light response, grouped means were plotted as percent BOLD signal change versus trial number for the red light placebo and drug conditions (FIG. 5). When linear regression analysis was used to determine if there was an effect of time following drug administration on the BOLD signal response to red light, there was no significant effect of drug over time (Z=−0.470, P=0.638). Similarly, there was no effect of time on BOLD signal response following placebo administration (Z=−0.880, P=0.379).

The results of the drug trial indicate that while the overall BOLD response to red and blue light is enhanced by low dose d-amphetamine administration, the blue light response shows a differential sensitivity to drug administration. Specifically, the mean photic stimulation-elicited BOLD signal intensity changes across all trials were higher for blue and for red light in the drug versus the placebo condition. Secondly, there was no effect of time on the red light elicited BOLD signal, but there was a clear time-related peak and decline in blue light evoked BOLD signal over time. More specifically, at early time points following drug administration, there was a large enhancement of the BOLD response to blue light that decayed over time yielding to a persistent lower-level augmentation. Thus, the blue light response was more directly influenced by changes in amphetamine-induced dopamine release than was the red light response. The early transient augmentation in V1 BOLD signal in response to blue light is likely mediated via a decrease in dopamine release produced by the inhibitory action of dopamine at autoreceptors. As blood levels increase over time, this effect would decay, and would give way to a sustained effect of the higher drug level, likely dominated by increased dopamine release. This idea is consistent with the early onset and transient nature of the blue light response. The hemodynamic effects of d-amphetamine are constant and common to both colors of light. Therefore, the transient augmentation of the V1 BOLD response to blue light is largely neuronal in origin.

The sustained augmentation of BOLD signal change reflects hemodynamic, vascular, and neuronal alterations common to both the red and blue light sensory pathways. At the hemodynamic level, d-amphetamine produces dose-dependent increases in cardiac output. Peripheral blood pressure increases due to combined changes in cardiac output and increased peripheral resistance via a vasoconstrictive mechanism, which will likely be modest at the doses used in this study. Within the brain, dopaminergic axons (of presumed neuronal origin) directly innervate cerebral microvasculature, and direct application of dopamine to these vessels leads to vasoconstriction. This finding are of significance in humans; for example, the potent vasoconstrictor cocaine produces an increase in BOLD signal in visual cortex in a photic stimulation paradigm and ethanol inhibits photic activation with a similar paradigm. These effects are partially mediated though direct dopaminergic innervation of the vasculature.

Thus, this study demonstrates that very low dose amphetamine produces a general increase in the BOLD response to a fixed stimulus. This effect can be exploited to enhance fMRI signal to detect regional BOLD signal changes that were previously below the level of detectability at baseline for a wide variety of experimental paradigms. Second, the current findings indicate that spontaneously occurring variations in transmitter-specificity among sensory receptors can allow for selective manipulation of transmitter-dependent aspects of a stimulus. In addition, the observation of differential dopamine sensitivity for the blue light response indicates that this marker will co-vary with altered dopamine conditions such as schizophrenia, Parkinson's disease, and substance abuse.

The present findings further support the use of fMRI in pharmacological assessment of neurophysiology in health and illness. Analysis of both red and blue light responses provides a means to differentiate vascular and neuronal effects of dopaminergic manipulations. Using a volume head coil will also offer the opportunity to assess, for example, the LGN response to amphetamine in parallel with the cortical response. Including drug level measurements in such analyses will further enable diagnosis and therapy of neurotransmitter based functional alterations in humans.

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the appended claims.

Other embodiments are within the claims.

What is claimed is:

1. A method of assessing central nervous system function in a human subject, said method comprising the steps of:
    (a) subjecting said subject to a blue light stimulus; and
    (b) performing cortical imaging on said subject.

2. The method of claim 1, further comprising treating said subject with a therapeutic agent for affecting central nervous system dopamine function, wherein said method is used to assess the efficacy of said agent.

3. The method of claim 1, further comprising diagnosing a central nervous system disorder in said human subject.

4. The method of claim 1 or 2, wherein said blue light stimulus is compared to a light stimulus of another color.

5. The method of claim 4, wherein said light stimulus of another color is a red light stimulus.

6. The method of claim 3, wherein said central nervous system disorder comprises a disorder of central nervous system dopamine function.

7. The method of claim 3, wherein said central nervous system disorder is selected from the group consisting of schizophrenia, Parkinson's disease, and attention deficit hyperactivity disorder.

8. The method of claim 1, wherein said cortical imaging is selected from the group consisting of functional magnetic resonance imaging, near infrared optical imaging, and emission tomography.

9. The method of claim 3, wherein said central nervous system disorder is selected from the group consisting of a mood and anxiety disorder and substance abuse.

10. The method of claim 9, wherein said mood and anxiety disorder is selected from the group consisting of major depression and bipolar disorder.

11. The method of claim 1, wherein said blue light stimulus is exposed to an eye of said human subject.

12. The method of claim 1, wherein said blue light stimulus results in stimulation of the subject's visual cortex.

13. The method of claim 1, wherein said cortical imaging is performed using magnetic resonance imaging (MRI).

* * * * *